US006197808B1

(12) United States Patent
Cheng et al.

(10) Patent No.: US 6,197,808 B1
(45) Date of Patent: *Mar. 6, 2001

(54) METHODS FOR TREATING HYPERPLASIA

(75) Inventors: Shu Jun Cheng; De Chang Wang, both of Beijing (CN); Yukihiko Hara, Fujieda (JP); Insu P. Lee; Woong Shick Ahn, both of Seoul (KR)

(73) Assignees: Cancer Instititute (Hospital), Chinese Academy of Medical Sciences, Beijing (CN); Mitsui Norin Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/418,890

(22) Filed: Oct. 15, 1999

Related U.S. Application Data

(63) Continuation-in-part of application No. 09/056,378, filed on Apr. 7, 1998, now Pat. No. 5,968,973, which is a continuation-in-part of application No. 08/835,920, filed on Apr. 10, 1997, now Pat. No. 5,795,911.

(30) Foreign Application Priority Data

Sep. 15, 1997 (JP) ................................................ 9-321195

(51) Int. Cl.$^7$ ................................................... A61K 31/35
(52) U.S. Cl. ............................................................ 514/456
(58) Field of Search ................................................ 514/456

(56) References Cited

U.S. PATENT DOCUMENTS

| 5,135,957 | * | 8/1992 | Shimamura . |
| 5,159,069 | * | 10/1992 | Hirayama et al. . |
| 5,211,944 | * | 5/1993 | Tempesta . |
| 5,576,013 | * | 11/1996 | Williams et al. . |
| 5,605,929 | * | 2/1997 | Bombardelli et al. . |
| 5,648,377 | | 7/1997 | Bombardelli et al. . |
| 5,795,911 | * | 8/1998 | Cheng et al. ................. 514/456 |

FOREIGN PATENT DOCUMENTS

| 22 06 570 | 9/1972 | (DE) . |
| 42 11 238 | 10/1993 | (DE) . |
| 0 417 385 | 3/1991 | (EP) . |
| 2 293 548 | 4/1996 | (GB) . |
| WO 96/28178 | 9/1996 | (WO) . |

OTHER PUBLICATIONS

Database WPI, Week 9130, Derwent Publications Ltd., London GB; AN 91–21971, Abstract of JP 03 141 220 A (Tsumura & Co.), Jun. 17, 1991.

Stich et al., "The effect of retinoids carotenoids and phenolics on chromosomal instability of bovine papillomavirus DNA–carrying cells", *Mutation Research*, vol 241, No. 4 (1990), pp. 387–393.

Mukhtar et al., "Green Tea and Skin–Anticarcinogenic Effects", The Society for Investigative Dermatology, Inc., vol. 102, No. 1 (1994), pp. 3–7.

Hirose et al., "Inhibition of mammary gland carcinogenesis by green tea tatechins and other naturally occurring antioxidants in female Sprague–Dawley rats pretreated with 7,12–dimethylbenz[α]anthracene", *Cancer Letters*, vol. 83, No. 1–2 (1994), pp. 149–156.

\* cited by examiner

*Primary Examiner*—James H. Reamer
(74) *Attorney, Agent, or Firm*—Frishauf, Holtz, Goodman, Langer & Chick, P.C.

(57) ABSTRACT

A method for a treatment of hyperplasia caused by papilloma virus, such as *Condyloma acuminata*, which comprises concomitantly topically and orally administering at least one tea catechin. Tea catechins do not involve the risk of side-effects and may be easily administered by the patients themselves.

21 Claims, No Drawings

METHODS FOR TREATING HYPERPLASIA

The present application is a continuation-in-part application of application Ser. No. 09/056,378 filed Apr. 7, 1998 (now U.S. Pat. No. 5,968,873), which is a continuation-in-part application of application Ser. No. 08/835,920 filed Apr. 10, 1997 (now U.S. Pat. No. 5,795,911).

BACKGROUND OF THE INVENTION

FIELD OF THE INVENTION

The present invention relates to methods for treating the hyperplasia caused by a papilloma virus, such as Condyloma epithelial cells of mammals and which causes uncontrolled cell replication. There are many types of papilloma virus which infect human and animal species, but they all can infect the basal epithelial cells and persist in an episome or as DNA integrated into the host genome. The mechanism by which they cause tissue growth may be related to the E4 and E5 proteins they all produce in related forms, which appear to interact with p54 and other host proteins which control the cell cycle. The effects of papilloma virus which have been described include genital warts or *Condylomata acuminate*, common warts, plantar warts, bovine papillomas, and cervical intra-epithelial neoplasia in women.

The detection of human papilloma virus ("HPV") in *Condyloma acuminata* involve a method of taking a tissue sample or a smear from the infected area and determining the DNA of the virus. According to this method, the detection rate is almost 100%.

Types HPV6 and 11 of the virus are the ones most commonly detected and because HPV16 has been detected in malignant squamous cell carcinoma from cancer of the penis, cancer of the cervix and *Condyloma acuminata*, there is a strong possibility that HPV16 is related to the malignancy of *Condyloma acuminata*.

Means for the treatment of *Condyloma acuminata* caused by human papilloma virus which have been tried include physical means such as surgical excision, electrocauterization, cryosurgery, laser therapy, etc., and medications such as applications of Podophyllin, 5-Fluorouracil, Bleomycin, Interferon, Imiquimod, etc., which are presently available. However, surgical treatment is distressing for the patient, considering the site of infection, and with topical applications there is the concern of side-effects. The aforesaid medications work either by cytotoxic tissue destruction or by enhancing the cellular immune response by causing local inflammation. Accordingly, a conclusive treatment has heretofore not been available.

*Condyloma acuminata* has a high rate of recurrence, and a complete cure is difficult unless treated constantly. Therefore, a treatment which has a high degree of safety and is convenient is strongly desired.

A treatment regimen for hyperplasia caused by a papilloma virus, such as *Condyloma acuminata*, which would be easy for the patient to administer, is desired. For example, it would desirable to have a medication which can be taken orally and can be applied to the affected area by the patients themselves and which would provide good results after a relatively short period of use and have no side-effects.

SUMMARY OF THE INVENTION

The present inventors searched for a natural substance which has no side-effects, may be safely applied for a long period of time by the patients themselves and is notably effective. After extensive testing, the inventors discovered that catechin, a component of tea which is an everyday beverage, is effective for treating hyperplasia caused by papilloma virus, and thus the present invention was developed.

Accordingly, the present invention relates to a method for the treatment of hyperplasia caused by papilloma virus, comprising concomitantly orally and topically administering to a human an effective anti-hyperplasia amount of a tea extract containing catechin as a main component. More specifically, the present invention concerns the treatment of hyperplasia caused by a papilloma virus such as *Condyloma acuminata*, common warts, plantar warts and cervical infra-epithelial neoplasia by a combination of topical administration of at least one tea catechin and oral administration of at least one tea catechin.

DETAILED DESCRIPTION OF THE INVENTION

The tea catechins for use in the present invention are shown below in the following formula I

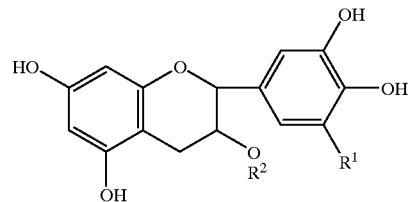

wherein $R^1$ represents H or OH and $R^2$ represents H or

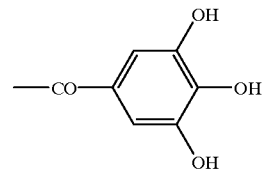

The tea catechins are more specifically, epicatechin, epicatechin gallate, epigallocatechin gallate, gallocatechin, etc. (including derivatives thereof). These catechins can be used singly, or two or more may be mixed together. Out of these it is particularly desirable to have (–)-epigallocatechin gallate as a main component. Examples of tea catechin compositions for use in the present invention include the following: POLYPHENON 100™ (produced by Mitsui Norin Co.; Composition: (+)-gallocatechin 1.44 wt %, (–)-epicatechin 5.81 wt %, (–)-epigallocatechin 17.57 wt %, (–)-epicatechin gallate 12.51 wt %, (–)-epigallocatechin gallate 53.90 wt %; or POLYPHENON E™ (produced by Mitsui Norin Co.; Composition: (–)-epicatechin 10.8 wt %, (–)-epigallocatechin 9.2 wt %, (–)-epicatechin gallate 6.5 wt %, (–)-epigallocatechin gallate 54.8 wt %, (–)-gallocatechin gallate 4.0 wt %).

The formulations for the topical administration of the tea catechin compounds or tea catechin composition employed for the treatment of hyperplasia according to the present invention can be, for example, in the form of an ointment such as a cream, a jelly, or an emulsion; or in the form of a suppository such as a capsule, and usually the tea catechin component is combined with an excipient, an extending agent, an emulsifier, a dispersing agent, etc. Vaseline is suitable as a base for the ointment. For the ointment, the content of tea catechin should be between 2 to 20% by weight, preferably between 12 to 18% by weight, and more preferably 15% by weight. In the case of a suppository, the content of tea catechin should be 50 to 500 mg/capsule, preferably 200 to 300 mg/capsule, or more preferably 250 mg/capsule.

A typical usage example for the ointment is to apply the ointment directly to the infected area of the external genital organs or vagina, a vaseline cream containing 2 to 20% by weight catechin, from once to several times everyday for a period of 1 to 2 months. A typical usage example for the suppository in the case where, for example, the infected area is the cervix or the vagina, is to insert a capsule containing 50 to 500 mg tea catechin, from once to several times everyday for a period of 1 to 2 months.

There is no danger of side-effects from the use of tea catechins for the treatment of hyperplasia, since the tea catechins are natural substances derived from tea, which is commonly consumed regularly, and it may be taken for long periods of time. Moreover, for topical administration, this medication may be easily applied to or inserted in the infected area by the patients themselves. The composition of the present invention for a treatment of hyperplasia has a very high potential for practical use.

The formulations for oral administration of the tea catechin compounds or tea catechin composition utilized in the present invention can be, for example, in the form of tablets, capsules, granules, powders or syrups. The pharmaceutical preparations for oral administration can be produced in a conventional manner using adjuvants that are generally known in the art, such as excipients, binders, disintegrating agents, lubricants, stabilizers, corrigents and the like. Although the dosage may vary depending upon the symptoms and age of the patient, the nature and severity of the disease or disorder, in the case of oral administration to an adult human patient, the tea catechin compounds used in the present invention may normally be administered at a total daily oral dose of from 100 to 2,000 mg, either in a single oral dose, or in divided oral doses, for example, two or three times a day.

EXAMPLES

The present invention will be explained in more detail with reference to the following examples which are in no way meant to limit the scope of the invention.

Test Example 1

An ointment consisting essentially of a vaseline based vaginal lubricant containing, as the main component, tea catechin (Trade name: "POLYPHENON 100", produced by Mitsui Norin Co. Ltd., its main component: (-)-epigallocatechin gallate) was applied to the cervix of healthy mice (50 mice in a group) in catechin dosages of 8 mg, 15 mg, and 38 mg for a period of 7 consecutive days. After this time, pathological and histological examinations were carried out and it was determined that except for a mild inflammatory reaction in the cervix of the group of mice administered with the 38 mg dose, no toxic effect was observed.

Example 1

Clinical tests of the present invention were carried out at the Cancer Institute, Chinese Academy of Medical Sciences in Beijing, China, with a group of 11 women who had been diagnosed with HPV-infected *Condyloma acuminate*. All patients were confirmed to have Condyloma in the vulva (external genital organs) and cervix according to clinical examination, cytologic, colposcopic and pathologic tests. Warts were from 0.2 to 2 cm in diameter.

Tests were carried out on these 11 patients using either a vaseline-based ointment containing 10 wt % of tea catechin (Trade name: "POLYPHENON 100", produced by Mitsui Norin co., Ltd., crude catechin content is about 90 weight % and its main component is (-)-epigallocatechin gallate) or using a suppository containing 300 mg/capsule of the above tea catechin. Applying the ointment to the external genital organs and applying the suppository to the cervix, the treatments of the present invention were used continuously once a day for about two months.

During the period of treatment, examinations and colposcopic tests of the infected areas were carried out. Results obtained are shown in Table 1. As shown in Table 1 hereinbelow, when the infected area completely disappeared it was judged to be cured, when 50% or more disappeared, it was judged to be improved and when less than 50% or nothing disappeared, it was judged that there was no effect.

TABLE 1

| Infected Area | No. of Patients | Cured | Improved | No Effect |
| --- | --- | --- | --- | --- |
| External genital organs | 9 | 4 | 3 | 2 |
| Cervix | 2 | 1 | 0 | 1 |

As is evident from Table 1, 7 cases out of 9 (77.8%) of *Condyloma acuminata* of the external genital organ showed a clear effect (being either cured or improved). In one case of the cervical infection, the tumor completely disappeared, and thus was cured. During this period, apart from some patients who experienced slight pain or inflammation in the infected area and a few other patients who felt some itching, there were no obvious side-effects observed.

Example 2

Clinical tests at the Cancer Institute, Chinese Academy of Medical Sciences in Beijing, China were conducted in the same manner as in Example 1, using a vaseline-based ointment containing 15 weight % tea catechin on external and internal warts, with a group of 33 female patients diagnosed with HPV-infected *Condyloma acuminata*. In this group, 8 of the patients were infected in two areas. The results are shown in Table 2 hereinbelow. As is evident from Table 2, 92% of *Condyloma acuminata* of the external genital organs and 70% of the vaginal *Condyloma acuminata* were cured or improved, and in the case of the cervical *Condyloma acuminata*, all cases were cured. 25 cases out of 41 cases showed were cured, and the curing ratio was 61%.

TABLE 2

| Infected Area | No. of Patients | Cured | Improved | No Effect |
| --- | --- | --- | --- | --- |
| External genital organs | 26 | 18 | 6 | 2 |
| Vagina | 10 | 2 | 5 | 3 |
| Cervix | 5 | 5 | 0 | 0 |
| Total (%) | 41 | 25 (61.0) | 11 (26.8) | 5 (12.2) |

Example 3

Clinical tests at the Cancer Institute, Chinese Academy of Medical Sciences in Beijing, China were conducted in the same manner as in Example 2, except that the ointment contained 15 weight % of a different tea extract ("POLYPHENOL E", produced by Mitsui Norin Co., Ltd., which is similar to "POLYPHENOL 100"; the crude catechin content of "POLYPHENOL E" is about 82 weight %, and its main component is (−)-epigallocatechin gallate) with a group of 22 female patients diagnosed with HPV-infected *Condyloma acuminata*. The results are shown in Table 3 hereinbelow. As is evident from Table 3, out of 16 cases of *Condyloma acuminata* of the external genital organs, 7 were cured and 6 improved; a total of 13 (81.3%) being effected. In the case of *Condyloma acuminata* of the vagina, out of 6 cases 3 were cured and 2 were improved; a total of 83.3% was confirmed to be effected.

TABLE 3

| Infected | No. of Patients | Cured | Improved | No Effect |
| --- | --- | --- | --- | --- |
| External genital organs | 16 | 7 | 6 | 3 |
| Vagina | 6 | 3 | 2 | 1 |
| Total (%) | 22 | 10 (45.5) | 8 (36.4) | 4 (18.2) |

Example 4

Clinical tests were carried out at the Department of Obstetrics & Gynecology, Kang Nam St. May's Hospital, Catholic University Medical Center, Catholic Medical College, Seoul, Korea.

A total of 41 patients diagnosed as cervical intraepithelial neoplasia I, II and III, including cervical cervicitis, were treated topically 2 times a week with the tea catechin ointment described in Example 3 for a duration of 8 weeks. Among these 41 subjects, 33 were treated with only topical application of the above-described ointment, while the remaining 8 subjects were orally given a tea catechin capsule (100 mg catechin/capsule) two times a day for 8 weeks, in addition to the topical application. The tea catechin capsule contained tea catechin of the following composition: 25 wt % epigallocatechin, 9 wt % epicatechin, 56 wt % epigallocatechin gallate and 13 wt % epicatechin gallate.

In order to determine the optimal topical application, preliminary tests were conducted to apply the tea catechin ointment to a lesion from two times a day to twice a week, and it was found that twice a week application induces just about the same results on the lesion as the more frequent applications.

All patients completed the requirements of pretreatment evaluation and consented to cytology, cervicography, colposcopy, HPV DNA analysis and cervical biopsy for histologic evaluation. Evaluation criteria were colposcopy, cervicography, cytology, histology, nuclear morphometry and HPV DNA analysis by PCR technology. The results in Table 4 below show a much higher response rate by the combination therapy, i.e., topical application and oral administration in combination, rather than topical application alone.

TABLE 4

| | No. of Patients | Responder | Non-Responder |
| --- | --- | --- | --- |
| Topical application | 33 | 19 (58%) | 14 (42%) |
| Topical application + oral administration | 8 | 6 (75%) | 2 (25%) |

The entire disclosure of Japanese Patent Application No. 8-321195 filed on Nov. 18, 1996, including the specification, claims and summary, is incorporated herein by reference in its entirety.

What is claimed is:

1. A method for treating hyperplasia caused by a papilloma virus comprising both topically and orally administering to a human in need thereof a composition which comprises at least one tea catechin in an effective antihyperplasia amount.

2. The method according to claim 1, wherein tea catechin comprises (−)-epigallocatechin gallate.

3. The method according to claim 1, wherein said composition for topical administration is in the form of an ointment.

4. The method according to claim 2, wherein said composition for topical administration is in the form of an ointment.

5. The method according to claim 1, wherein said composition for topical administration is in the form of a suppository.

6. The method according to claim 2, wherein said composition for topical administration is in the form of a suppository.

7. The method of claim 3, wherein the tea catechin is in an amount of 2 to 20% by weight.

8. The method of claim 3, wherein the tea catechin is in an amount of 5 to 20% by weight.

9. The method of claim 3, wherein the tea catechin is in an amount of 15% by weight.

10. The method of claim 8, wherein the composition for topical administration comprises vaseline as a base to form a cream.

11. The method of claim 10, wherein the cream is topically applied to external genital organs.

12. The method of claim 5, wherein the suppository contains 50 to 500 mg by weight of the tea catechin.

13. The method of claim 5, wherein the suppository contains 200 to 300 mg by weight of the tea catechin.

14. The method of claim 5, wherein the suppository contains 250 mg of the tea catechin.

15. The method according to claim 13, wherein the suppository is applied to the vagina of a human.

16. The method of claim 1, wherein the composition is topically applied to an infected area on a human.

17. The method according to claim 16, wherein the infected area is the vagina.

18. The method according to claim 16, wherein the infected area is an external genital organ.

19. The method according to claim 16, wherein the infected area is the cervix.

20. The method according to claim 1, wherein the papilloma virus causes *Condyloma acuminata*.

21. The method according to claim 1, wherein the papilloma virus causes cervical intra-epithelial neoplasia.

\* \* \* \* \*

UNITED STATES PATENT AND TRADEMARK OFFICE
CERTIFICATE OF CORRECTION

PATENT NO. : 6,197,808 B1
DATED : March 6, 2001
INVENTOR(S) : Shu Jun Cheng et al.

It is certified that error appears in the above-identified patent and that said Letters Patent is hereby corrected as shown below:

Title page,
Item [30], Foreign Application Priority Data, replace "Sep. 15, 1997" with
-- Nov. 18, 1996 --.
Item [56], References Cited, U.S. PATENT DOCUMENTS, "5,605,929", reference replace "2/1997 Bombardelli et al." with -- 2/1997 Liao et al. --.

Signed and Sealed this

Twenty-seventh Day of January, 2004

JON W. DUDAS
*Acting Director of the United States Patent and Trademark Office*